US010123966B2

(12) United States Patent
Mahmud et al.

(10) Patent No.: US 10,123,966 B2
(45) Date of Patent: Nov. 13, 2018

(54) HAIR THICKENING COMPOSITIONS AND METHODS OF USE

(71) Applicant: The Procter & Gamble Company, Cincinnati, OH (US)

(72) Inventors: Goher Mahmud, Mason, OH (US); Mary Jane Combs, Covington, KY (US)

(73) Assignee: The Procter and Gamble Company, Cincinnati, OH (US)

( * ) Notice: Subject to any disclaimer, the term of this patent is extended or adjusted under 35 U.S.C. 154(b) by 154 days.

(21) Appl. No.: 14/275,196

(22) Filed: May 12, 2014

(65) Prior Publication Data

US 2014/0341832 A1   Nov. 20, 2014

Related U.S. Application Data

(60) Provisional application No. 61/824,196, filed on May 16, 2013.

(51) Int. Cl.
*A61K 8/9789* (2017.01)
*A61K 36/185* (2006.01)
*A61K 8/81* (2006.01)
*A61Q 5/00* (2006.01)
*A61Q 7/00* (2006.01)
*A61K 8/97* (2017.01)

(52) U.S. Cl.
CPC .......... *A61K 8/9789* (2017.08); *A61K 8/8158* (2013.01); *A61K 8/97* (2013.01); *A61K 36/185* (2013.01); *A61Q 5/002* (2013.01); *A61Q 7/00* (2013.01)

(58) Field of Classification Search
None
See application file for complete search history.

(56) References Cited

U.S. PATENT DOCUMENTS

| 85,311 A | 12/1868 | Kerr et al. |
| 665,608 A | 1/1901 | Kotz |
| 724,178 A | 3/1903 | Grant |
| 812,241 A | 2/1906 | Shubert |
| 1,064,901 A | 6/1913 | Grosert |
| 1,384,671 A | 7/1921 | Murray |
| 1,431,943 A | 10/1922 | Gee |
| 1,462,400 A | 7/1923 | Warren |
| 1,829,021 A | 10/1931 | Sinclair |
| 1,876,033 A | 9/1932 | Starr |
| 1,956,769 A | 5/1934 | Maselli |
| 2,031,774 A | 2/1936 | Lewis et al. |
| 2,118,566 A | 5/1938 | Miles |
| 2,171,494 A * | 8/1939 | Kyrides ............... C07C 37/002 568/322 |
| 2,293,634 A | 8/1942 | Sluss |
| 2,381,048 A | 8/1945 | Arne |
| 2,604,102 A | 7/1952 | Krause |
| 2,647,490 A | 8/1953 | Twiet |
| 2,794,443 A | 6/1957 | Moore |
| 2,809,971 A | 10/1957 | Bernstein |
| 2,826,551 A | 3/1958 | Geen |
| 3,101,086 A | 8/1963 | Di Vito |
| 3,204,644 A | 9/1965 | Flora |
| 3,236,733 A | 2/1966 | Karsten |
| 3,295,537 A | 1/1967 | Young |
| 3,457,928 A | 7/1969 | Kurshenoff |
| 3,463,170 A | 8/1969 | McCullough |
| 3,477,447 A | 11/1969 | Eldredge |
| 3,520,311 A | 7/1970 | Iesersek et al. |
| 3,575,319 A | 4/1971 | Safianoff |
| 3,658,294 A | 4/1972 | Ewald |
| 3,730,182 A | 5/1973 | Boghosian |
| 3,732,591 A | 5/1973 | Gach |
| 3,753,196 A | 8/1973 | Kurtz et al. |
| 3,755,560 A | 8/1973 | Dickert et al. |
| 3,761,418 A | 9/1973 | Parran |
| 3,960,160 A | 6/1976 | Hogan |
| 3,961,635 A | 6/1976 | Miya |
| 3,964,500 A | 6/1976 | Drakoff |
| 4,090,647 A | 5/1978 | Dunning |
| 4,121,602 A | 10/1978 | Young |
| 4,144,325 A | 3/1979 | Voyt |
| 4,152,416 A | 5/1979 | Spitzer et al. |
| 4,209,027 A | 6/1980 | Morganroth |
| 4,273,144 A | 6/1981 | Morganroth |
| 4,288,433 A | 9/1981 | Koulbanis et al. |
| 4,323,683 A | 4/1982 | Bolich, Jr. et al. |
| 4,324,553 A | 4/1982 | Bugaut et al. |
| 4,335,103 A | 6/1982 | Barker et al. |
| 4,345,080 A | 8/1982 | Bolick, Jr. |
| 4,354,512 A | 10/1982 | Roppatte, Jr. |
| 4,364,837 A | 12/1982 | Pader |
| 4,379,753 A | 4/1983 | Bolich, Jr. |
| 4,421,769 A | 12/1983 | Dixon et al. |
| 4,470,982 A | 9/1984 | Winkler |
| 4,495,958 A | 1/1985 | Roeder |
| 4,590,687 A | 5/1986 | Caruso |
| 4,602,651 A | 7/1986 | Roppatte, Jr. |

(Continued)

FOREIGN PATENT DOCUMENTS

| BR | 8802728 U | 8/2010 |
| CA | 0944695 A1 | 4/1974 |

(Continued)

OTHER PUBLICATIONS

PCT International Search Report and Written Opinion for PCT/US2014/037617 dated Oct. 6, 2014, 12 pages.

(Continued)

*Primary Examiner* — John Pak
*Assistant Examiner* — Daniel L Branson
(74) *Attorney, Agent, or Firm* — Alexandra S. Anoff

(57) ABSTRACT

Provided is a method for increasing hair shaft diameter, the method including applying a hair care composition to a region of the hair, wherein the hair care composition includes from about 0.01% to about 10% of hops, wherein the hops is first extracted in glycerin; and from about 0.1% to about 10% of a rheology modifier.

10 Claims, No Drawings

(56) References Cited

U.S. PATENT DOCUMENTS

| | | |
|---|---|---|
| 4,605,026 A | 8/1986 | Nolin |
| 4,671,306 A | 6/1987 | Spector |
| 4,733,984 A | 3/1988 | Katsuda et al. |
| 4,815,637 A | 3/1989 | Nellis |
| 4,872,594 A | 10/1989 | Bloom |
| 4,900,545 A | 2/1990 | Wisotzki et al. |
| 4,901,891 A | 2/1990 | Goncalves |
| 4,934,388 A | 6/1990 | Gibbs |
| 4,983,383 A | 1/1991 | Maksimoski et al. |
| 5,006,004 A | 4/1991 | Dirksing et al. |
| 5,041,285 A | 8/1991 | Lundmark |
| 5,043,323 A | 8/1991 | Bombardelli et al. |
| 5,054,504 A | 10/1991 | Winrow |
| 5,056,480 A | 10/1991 | Murray, Sr. |
| 5,059,050 A | 10/1991 | Guglielmo |
| 5,069,898 A | 12/1991 | Goldberg |
| 5,104,646 A | 4/1992 | Bolich, Jr. et al. |
| 5,106,609 A | 4/1992 | Bolich, Jr. et al. |
| 5,152,305 A | 10/1992 | Niv |
| 5,168,833 A | 12/1992 | Spears |
| 5,215,759 A | 6/1993 | Mausner |
| 5,227,164 A | 7/1993 | Lundmark |
| 5,227,503 A | 7/1993 | Hagan et al. |
| 5,261,427 A | 11/1993 | Dolev |
| 5,270,035 A | 12/1993 | Chimento |
| RE34,584 E | 4/1994 | Grote et al. |
| 5,301,850 A | 4/1994 | Gueret |
| 5,307,964 A | 5/1994 | Toth |
| 5,311,887 A | 5/1994 | Ramsey |
| 5,337,764 A | 8/1994 | McKay |
| 5,340,570 A | 8/1994 | Wong et al. |
| 5,364,885 A | 11/1994 | Ahluwalia et al. |
| 5,469,286 A | 11/1995 | Nicole |
| 5,470,579 A | 11/1995 | Bonte et al. |
| 5,502,056 A | 3/1996 | Breitbarth |
| 5,514,374 A | 5/1996 | Bonte et al. |
| 5,520,918 A | 5/1996 | Smith |
| D370,783 S | 6/1996 | Korte |
| 5,523,078 A | 6/1996 | Baylin |
| 5,555,899 A | 9/1996 | Foreman |
| 5,605,257 A | 2/1997 | Beard |
| 5,637,606 A | 6/1997 | Matsumoto |
| 5,641,097 A | 6/1997 | Renault et al. |
| 5,647,606 A | 7/1997 | Jordan |
| 5,649,649 A | 7/1997 | Marelli |
| 5,658,575 A | 8/1997 | Ribier et al. |
| 5,686,082 A | 11/1997 | N'Guyen |
| 5,686,367 A | 11/1997 | Hayashi |
| 5,687,884 A | 11/1997 | Bodin et al. |
| 5,702,691 A | 12/1997 | Ichinose et al. |
| D392,887 S | 3/1998 | Wadsworth |
| 5,738,250 A | 4/1998 | Gillingham et al. |
| 5,746,348 A | 5/1998 | Bloom |
| 5,750,122 A | 5/1998 | Evans et al. |
| 5,755,241 A | 5/1998 | Cheung |
| 5,765,601 A | 6/1998 | Wells et al. |
| 5,772,077 A | 6/1998 | Tafur |
| 5,803,093 A | 9/1998 | Romano |
| 5,848,598 A | 12/1998 | Walz et al. |
| 5,876,703 A | 3/1999 | Ichinose et al. |
| 5,937,873 A | 8/1999 | Schlosser et al. |
| 5,939,082 A | 8/1999 | Oblong et al. |
| 5,957,342 A | 9/1999 | Gallien |
| 5,958,436 A | 9/1999 | Hahn et al. |
| D415,427 S | 10/1999 | Durliat |
| 5,964,226 A | 10/1999 | Sobel |
| 5,965,564 A | 10/1999 | Bianco et al. |
| 5,975,378 A | 11/1999 | Bayer |
| 5,975,381 A | 11/1999 | Revenu |
| D419,446 S | 1/2000 | Durliat |
| 6,013,270 A | 1/2000 | Hargraves et al. |
| 6,013,279 A | 1/2000 | Klett-Loch |
| 6,015,549 A | 1/2000 | Cowperthwaite et al. |
| 6,035,806 A | 3/2000 | Lorenzo |
| D424,938 S | 5/2000 | Wise |
| 6,113,926 A | 9/2000 | Soler et al. |
| 6,120,779 A | 9/2000 | Nayak et al. |
| 6,158,617 A | 12/2000 | Hershey et al. |
| 6,161,735 A | 12/2000 | Uchiyama et al. |
| 6,192,047 B1 | 2/2001 | Oota |
| 6,202,899 B1 | 3/2001 | Lasserre et al. |
| 6,239,170 B1 | 5/2001 | Ahluwalia et al. |
| 6,260,557 B1 | 7/2001 | Yarbrough |
| 6,277,360 B1 | 8/2001 | Carew et al. |
| 6,286,518 B1 | 9/2001 | Laporte |
| 6,302,607 B1 | 10/2001 | Burrowes et al. |
| 6,318,595 B1 | 11/2001 | Walters |
| 6,322,778 B1 | 11/2001 | Parr et al. |
| 6,325,070 B1 | 12/2001 | Tyroler et al. |
| 6,334,449 B1 | 1/2002 | Burrowes et al. |
| 6,357,449 B1 | 3/2002 | Chu et al. |
| 6,369,117 B1 | 4/2002 | Dubief et al. |
| 6,414,017 B2 | 7/2002 | Ahluwalia et al. |
| 6,444,647 B1 | 9/2002 | Robinson et al. |
| 6,447,762 B1 | 9/2002 | Casado Galcera |
| 6,465,421 B1 | 10/2002 | Duranton et al. |
| D466,017 S | 11/2002 | Kuo |
| 6,495,498 B2 | 12/2002 | Niemiec et al. |
| 6,505,983 B1 | 1/2003 | Seo |
| 6,526,987 B1 | 3/2003 | Gioia |
| 6,539,949 B2 | 4/2003 | Christensen |
| 6,570,010 B2 | 5/2003 | Ishida et al. |
| 6,588,964 B1 | 7/2003 | Au et al. |
| 6,637,440 B2 | 10/2003 | de Laforcade |
| 6,649,155 B1 | 11/2003 | Dunlop et al. |
| 6,660,047 B1 | 12/2003 | Stanley, III |
| 6,675,812 B1 | 1/2004 | Wiley |
| 6,752,157 B2 | 6/2004 | Lu Shao Hua |
| 6,766,806 B2 | 7/2004 | Thiebaut |
| D499,966 S | 12/2004 | Arminak |
| 6,831,107 B2 | 12/2004 | Dederen |
| 6,858,216 B2 | 2/2005 | Schulze zur Wiesche et al. |
| 6,861,061 B2 | 3/2005 | Maxon et al. |
| 6,866,167 B2 | 3/2005 | Bougamont |
| 6,877,924 B1 | 4/2005 | Mears et al. |
| 6,908,889 B2 | 6/2005 | Niemiec et al. |
| 6,962,158 B1 | 11/2005 | Anguelo |
| 6,968,849 B2 | 11/2005 | Vena et al. |
| 6,976,495 B2 | 12/2005 | Vena et al. |
| 6,994,846 B2 | 2/2006 | L'Alloret |
| 7,000,618 B2 | 2/2006 | Dovergne et al. |
| 7,044,137 B2 | 5/2006 | Glucksman et al. |
| 7,067,529 B2 | 6/2006 | Bolin et al. |
| 7,077,295 B2 | 7/2006 | Walker |
| 7,081,258 B2 | 7/2006 | Hwang et al. |
| 7,081,259 B2 | 7/2006 | Hong |
| D534,425 S | 1/2007 | Kuo |
| 7,196,055 B2 | 3/2007 | Gilchrest et al. |
| 7,234,239 B2 | 6/2007 | Saito et al. |
| 7,243,660 B2 | 7/2007 | Capristo |
| 7,258,852 B2 | 8/2007 | Maubru |
| 7,278,590 B1 | 10/2007 | Greer, Jr. et al. |
| 7,285,294 B2 | 10/2007 | Ishino et al. |
| 7,294,641 B2 | 11/2007 | Boulle et al. |
| D574,707 S | 8/2008 | Pietrowski et al. |
| 7,409,957 B2 | 8/2008 | Abergel |
| 7,470,657 B2 | 12/2008 | Guillou et al. |
| 7,473,435 B2 | 1/2009 | Koganov |
| 7,514,474 B1 | 4/2009 | Lipkin et al. |
| 7,537,791 B2 | 5/2009 | Koganov |
| 7,550,137 B2 | 6/2009 | Savaide et al. |
| D605,953 S | 12/2009 | Wang Treadway et al. |
| 7,647,933 B2 | 1/2010 | Morgenstern et al. |
| 7,690,535 B2 | 4/2010 | Law et al. |
| 7,754,775 B2 | 7/2010 | Mercier et al. |
| D620,807 S | 8/2010 | Wang Treadway et al. |
| 7,790,768 B2 | 9/2010 | Gan et al. |
| 7,798,154 B2 | 9/2010 | De Laforcade |
| 7,814,917 B2 | 10/2010 | Hurwitz |
| 7,820,636 B2 | 10/2010 | Okuda et al. |
| 7,871,599 B2 | 1/2011 | Khoshdel et al. |
| D636,261 S | 4/2011 | Michitsuji et al. |
| 7,934,512 B2 | 5/2011 | Spagnuolo |
| 7,934,626 B2 | 5/2011 | Choi et al. |

(56) References Cited

U.S. PATENT DOCUMENTS

| | | |
|---|---|---|
| 7,934,667 B2 | 5/2011 | Westrich |
| 7,972,075 B2 | 7/2011 | Tajima |
| 8,047,735 B2 | 11/2011 | Broadley et al. |
| 8,109,415 B2 | 2/2012 | Tu |
| 8,118,036 B2 | 2/2012 | Wang et al. |
| 8,232,317 B2 | 7/2012 | Gan et al. |
| 8,316,863 B2 | 11/2012 | De Laforcade et al. |
| 8,336,558 B2 | 12/2012 | Hurwitz |
| 8,348,897 B2 | 1/2013 | Shih et al. |
| D675,939 S | 2/2013 | Van Gogh |
| D681,876 S | 5/2013 | Still |
| 8,475,510 B2 | 7/2013 | Simon et al. |
| D690,876 S | 10/2013 | Murdock et al. |
| 8,637,569 B2 | 1/2014 | Birbara |
| 8,784,907 B2 | 7/2014 | Richards et al. |
| 9,050,407 B2 | 6/2015 | Shih et al. |
| 9,242,123 B2 | 1/2016 | Mahmud et al. |
| 9,402,792 B2 | 8/2016 | Mahmud et al. |
| 9,554,979 B2 | 1/2017 | Combs et al. |
| 9,610,233 B2 | 4/2017 | Mahmud et al. |
| 9,649,271 B2 | 5/2017 | Mahmud et al. |
| 9,730,953 B2 | 8/2017 | Birbara |
| 2001/0003583 A1 | 6/2001 | Montanari et al. |
| 2001/0012928 A1 | 8/2001 | Watabe |
| 2001/0018920 A1 | 9/2001 | De Laforcade |
| 2001/0031281 A1 | 10/2001 | kung et al. |
| 2001/0042553 A1 | 11/2001 | Duqueroie |
| 2002/0001605 A1 | 1/2002 | Carew et al. |
| 2002/0020421 A1 | 2/2002 | Vayrette |
| 2002/0034485 A1 | 3/2002 | Noser et al. |
| 2002/0056733 A1 | 5/2002 | Lasserre |
| 2002/0114770 A1 | 8/2002 | Bradley et al. |
| 2002/0139383 A1 | 10/2002 | Christensen |
| 2002/0158084 A1 | 10/2002 | Herring et al. |
| 2002/0183297 A1 | 12/2002 | Niazi |
| 2002/0197289 A1 | 12/2002 | Chevalier et al. |
| 2003/0003073 A1 | 1/2003 | Muller |
| 2003/0039619 A1 | 2/2003 | Bunger et al. |
| 2003/0049212 A1 | 3/2003 | Robinson et al. |
| 2003/0050201 A1 | 3/2003 | Guillou et al. |
| 2003/0059392 A1 | 3/2003 | L'Alloret |
| 2003/0068297 A1 | 4/2003 | Jain |
| 2003/0069618 A1 | 4/2003 | Smith, III et al. |
| 2003/0091521 A1 | 5/2003 | Midha et al. |
| 2003/0108577 A1 | 6/2003 | Lorant et al. |
| 2003/0108578 A1 | 6/2003 | Maubru |
| 2003/0157088 A1 | 8/2003 | Elliott et al. |
| 2003/0168476 A1 | 9/2003 | Sanchez |
| 2003/0175232 A1 | 9/2003 | Elliott et al. |
| 2003/0219392 A1 | 11/2003 | Kung et al. |
| 2004/0076654 A1 | 4/2004 | Vinson et al. |
| 2004/0131573 A1 | 7/2004 | Tang |
| 2004/0141935 A1 | 7/2004 | Styczynski et al. |
| 2004/0159326 A1 | 8/2004 | Fagerstrom et al. |
| 2004/0171693 A1 | 9/2004 | Gan et al. |
| 2004/0175347 A1 | 9/2004 | Bissett |
| 2004/0213859 A1 | 10/2004 | Zelickson |
| 2004/0214215 A1 | 10/2004 | Yu et al. |
| 2004/0223935 A1 | 11/2004 | Meunier |
| 2004/0241114 A1 | 12/2004 | Gupta |
| 2005/0000535 A1 | 1/2005 | Kim |
| 2005/0003024 A1 | 1/2005 | Oblong et al. |
| 2005/0031572 A1 | 2/2005 | Gallinat et al. |
| 2005/0053561 A1 | 3/2005 | Suginaka |
| 2005/0082315 A1 | 4/2005 | Hayakawa et al. |
| 2005/0092340 A1 | 5/2005 | Rijskamp |
| 2005/0100525 A1 | 5/2005 | Taguchi et al. |
| 2005/0153003 A1 | 7/2005 | Menon et al. |
| 2005/0186290 A1 | 8/2005 | Cals-Grierson |
| 2005/0191370 A1 | 9/2005 | De La Charriere et al. |
| 2005/0196418 A1 | 9/2005 | Yu et al. |
| 2005/0255059 A1 | 11/2005 | Oblong et al. |
| 2005/0255060 A1 | 11/2005 | Oblong et al. |
| 2005/0271692 A1 | 12/2005 | Gervasio-Nugent et al. |
| 2006/0008436 A1 | 1/2006 | Boulle et al. |
| 2006/0021628 A1 | 2/2006 | Mu et al. |
| 2006/0021629 A1 | 2/2006 | Mu et al. |
| 2006/0039878 A1 | 2/2006 | Khoshdel et al. |
| 2006/0045926 A1 | 3/2006 | Nimni et al. |
| 2006/0054178 A1 | 3/2006 | Sim |
| 2006/0067905 A1 | 3/2006 | Lintner et al. |
| 2006/0088478 A1 | 4/2006 | Andrews et al. |
| 2006/0088492 A1 | 4/2006 | Goddinger et al. |
| 2006/0099167 A1 | 5/2006 | Staudigel et al. |
| 2006/0133997 A1 | 6/2006 | Querleux et al. |
| 2006/0134053 A1 | 6/2006 | L'Alloret |
| 2006/0151539 A1 | 7/2006 | Tsubaki et al. |
| 2006/0266774 A1 | 11/2006 | Hierzer |
| 2006/0275237 A1 | 12/2006 | Bissett et al. |
| 2006/0275245 A1 | 12/2006 | Decoster et al. |
| 2007/0003509 A1 | 1/2007 | Farwick et al. |
| 2007/0009474 A1 | 1/2007 | Xie et al. |
| 2007/0068544 A1 | 3/2007 | Hackl et al. |
| 2007/0080172 A1 | 4/2007 | Tyrrell et al. |
| 2007/0095360 A1 | 5/2007 | Meinert et al. |
| 2007/0095721 A1 | 5/2007 | Davis et al. |
| 2007/0137669 A1 | 6/2007 | Hamilton et al. |
| 2007/0148102 A1 | 6/2007 | Kalbfleisch et al. |
| 2007/0160547 A1 | 7/2007 | Duffy et al. |
| 2007/0175491 A1 | 8/2007 | Graefe et al. |
| 2007/0183993 A1 | 8/2007 | Binder et al. |
| 2007/0193597 A1 | 8/2007 | Hurwitz |
| 2007/0299032 A1 | 12/2007 | Ehama et al. |
| 2008/0020004 A1 | 1/2008 | Birkel et al. |
| 2008/0041749 A1 | 2/2008 | McDermott |
| 2008/0057015 A1 | 3/2008 | Oblong et al. |
| 2008/0059313 A1* | 3/2008 | Oblong ............... A61K 8/42 705/14.26 |
| 2008/0060665 A1 | 3/2008 | Umeno et al. |
| 2008/0064723 A1 | 3/2008 | Ideta et al. |
| 2008/0115796 A1 | 5/2008 | Montanari et al. |
| 2008/0206156 A1 | 8/2008 | Cronk |
| 2008/0206355 A1 | 8/2008 | Schwartz et al. |
| 2008/0207560 A1 | 8/2008 | Harada et al. |
| 2008/0213198 A1 | 9/2008 | Lintner et al. |
| 2008/0245380 A1 | 10/2008 | Ecker et al. |
| 2008/0245824 A1 | 10/2008 | Lyles |
| 2008/0249073 A1 | 10/2008 | Farwick et al. |
| 2008/0254055 A1 | 10/2008 | Oblong et al. |
| 2008/0317698 A1 | 12/2008 | Wells et al. |
| 2009/0000634 A1 | 1/2009 | Graefe et al. |
| 2009/0016970 A1 | 1/2009 | Cronk |
| 2009/0017147 A1 | 1/2009 | Lintner et al. |
| 2009/0039083 A1 | 2/2009 | Stull, Sr. et al. |
| 2009/0108023 A1 | 4/2009 | Houghton et al. |
| 2009/0208424 A1 | 8/2009 | Maibach et al. |
| 2009/0218418 A1 | 9/2009 | Sharief |
| 2009/0220445 A1 | 9/2009 | Iwata et al. |
| 2009/0220448 A1 | 9/2009 | Iwata et al. |
| 2009/0222350 A1 | 9/2009 | Iwata et al. |
| 2009/0264449 A1 | 10/2009 | Iwata |
| 2009/0274642 A1 | 11/2009 | Dawson, Jr. et al. |
| 2009/0275970 A1 | 11/2009 | Leibowitz |
| 2010/0012141 A1 | 1/2010 | Middlebrook |
| 2010/0018920 A1 | 1/2010 | Curran et al. |
| 2010/0083977 A1 | 4/2010 | Goddard-Clark et al. |
| 2010/0120871 A1 | 5/2010 | Dawson, Jr. et al. |
| 2010/0126522 A1 | 5/2010 | Fujinuma et al. |
| 2010/0137238 A1 | 6/2010 | Gan et al. |
| 2010/0161029 A1 | 6/2010 | Filippini et al. |
| 2010/0170917 A1 | 7/2010 | Ki |
| 2010/0218626 A1 | 9/2010 | Love et al. |
| 2010/0313905 A1 | 12/2010 | Fujinuma et al. |
| 2011/0005538 A1 | 1/2011 | Mercier et al. |
| 2011/0041863 A1 | 2/2011 | Roualdes |
| 2011/0064511 A1 | 3/2011 | Pires et al. |
| 2011/0110872 A1 | 5/2011 | Koganov et al. |
| 2011/0127293 A1 | 6/2011 | Pascatore |
| 2011/0232664 A1 | 9/2011 | Schreiber |
| 2011/0265805 A1 | 11/2011 | Laplante |
| 2012/0034173 A1 | 2/2012 | Batt et al. |
| 2012/0058060 A1 | 3/2012 | Noor et al. |
| 2012/0097180 A1 | 4/2012 | Harris et al. |
| 2012/0152270 A1 | 6/2012 | Hazan |

(56) References Cited

U.S. PATENT DOCUMENTS

| | | |
|---|---|---|
| 2012/0157478 A1 | 6/2012 | Dawson, Jr. et al. |
| 2012/0213842 A1 | 8/2012 | Birbara |
| 2012/0258185 A1 | 10/2012 | Oblong et al. |
| 2013/0133678 A1 | 5/2013 | Nakashima |
| 2013/0164390 A1 | 6/2013 | Dawson |
| 2013/0284195 A1 | 10/2013 | Murdock |
| 2013/0284196 A1 | 10/2013 | Murdock |
| 2013/0309332 A1 | 11/2013 | Fournial et al. |
| 2014/0093466 A1 | 4/2014 | Combs |
| 2014/0341832 A1 | 11/2014 | Mahmud et al. |
| 2014/0371690 A1 | 12/2014 | Sprada et al. |
| 2015/0314064 A1 | 11/2015 | Shih et al. |
| 2017/0296668 A1 | 10/2017 | Birbara |

FOREIGN PATENT DOCUMENTS

| | | |
|---|---|---|
| CN | 201261001 Y | 6/2009 |
| DE | 1914822 C3 | 7/1980 |
| DE | 4121544 A1 | 1/1993 |
| DE | 19824454 A1 | 12/1999 |
| DE | 10128799 A1 | 1/2003 |
| DE | 10133196 A1 | 1/2003 |
| DE | 10140650 A1 | 2/2003 |
| DE | 10226468 A1 | 1/2004 |
| DE | 10319227 A1 | 6/2004 |
| DE | 102004039729 A1 | 3/2006 |
| DE | 102004041588 | 3/2006 |
| DE | 202006002355 U1 | 4/2006 |
| DE | 20023828 U1 | 8/2006 |
| EP | 3259969 B1 | 4/1993 |
| EP | 0640333 A2 | 1/1995 |
| EP | 0943260 A1 | 9/1999 |
| EP | 1024091 A1 | 8/2000 |
| EP | 1097695 B1 | 9/2002 |
| EP | 1161934 B1 | 4/2004 |
| EP | 1430933 A2 | 6/2004 |
| EP | 1506767 A1 | 2/2005 |
| EP | 1308169 B1 | 6/2005 |
| EP | 1685826 A1 | 8/2006 |
| EP | 1700617 A1 | 9/2006 |
| EP | 1709956 A1 | 10/2006 |
| EP | 1771144 B1 | 7/2009 |
| EP | 1642565 B1 | 7/2010 |
| EP | 1676783 B1 | 11/2010 |
| FR | 2642941 A1 | 2/1981 |
| FR | 2580601 A1 | 10/1986 |
| FR | 2643375 B1 | 6/1991 |
| FR | 2751541 B1 | 10/1998 |
| FR | 2832062 B1 | 2/2004 |
| FR | 2930461 B1 | 12/2011 |
| GB | 849433 A1 | 9/1960 |
| GB | 2174356 A | 11/1986 |
| JP | S6168406 A | 4/1986 |
| JP | 6117945 A | 8/1986 |
| JP | 63301810 A | 12/1988 |
| JP | 63310813 A | 12/1988 |
| JP | H04189365 A | 7/1992 |
| JP | H04193821 A | 7/1992 |
| JP | H0597631 A | 4/1993 |
| JP | H06211632 A | 8/1994 |
| JP | H06234628 A | 8/1994 |
| JP | H08040835 A | 2/1996 |
| JP | H08073322 A | 3/1996 |
| JP | 2557390 B2 | 11/1996 |
| JP | 08291018 A | 11/1996 |
| JP | 10203924 A | 1/1997 |
| JP | 2583812 B2 | 2/1997 |
| JP | 09263534 A | 10/1997 |
| JP | 10053527 A | 2/1998 |
| JP | 10229978 A | 9/1998 |
| JP | H1027439 A | 10/1998 |
| JP | H10279437 A | 10/1998 |
| JP | H1118821 A | 1/1999 |
| JP | 11130085 A | 5/1999 |
| JP | H11130085 A | 5/1999 |
| JP | 11152213 A | 6/1999 |
| JP | 2000086449 A | 3/2000 |
| JP | 2000086510 | 3/2000 |
| JP | 3078179 B2 | 8/2000 |
| JP | 2001058928 A | 3/2001 |
| JP | 2001145514 A | 5/2001 |
| JP | 3219881 B2 | 10/2001 |
| JP | 2001288043 A | 10/2001 |
| JP | 2002013569 A | 1/2002 |
| JP | 2002322094 A | 11/2002 |
| JP | 2002332218 | 11/2002 |
| JP | 3400122 B2 | 4/2003 |
| JP | 3426436 B2 | 7/2003 |
| JP | 2004002264 | 1/2004 |
| JP | 2004026709 A | 1/2004 |
| JP | 2004067573 A | 3/2004 |
| JP | 2004091354 | 3/2004 |
| JP | 2004091370 A | 3/2004 |
| JP | 2004115465 | 4/2004 |
| JP | 2004189644 | 7/2004 |
| JP | 2004189645 A | 7/2004 |
| JP | 4133740 A | 5/2005 |
| JP | 2005225849 | 8/2005 |
| JP | 2005272394 A | 10/2005 |
| JP | 2005296352 A | 10/2005 |
| JP | 3784472 B2 | 6/2006 |
| JP | 2006160608 A | 6/2006 |
| JP | 3820800 B2 | 9/2006 |
| JP | 2006232820 | 9/2006 |
| JP | 3922311 B2 | 5/2007 |
| JP | 4173667 B2 | 10/2008 |
| JP | 2008230619 A | 10/2008 |
| JP | 4305756 B2 | 7/2009 |
| JP | 4469617 B2 | 5/2010 |
| JP | 4554805 B2 | 9/2010 |
| JP | 4574384 B2 | 11/2010 |
| JP | 5044069 | 10/2012 |
| JP | 5483414 B2 | 5/2014 |
| JP | 5872752 B2 | 3/2016 |
| SU | 1606121 A1 * | 11/1990 |
| WO | WO8804931 A1 | 7/1988 |
| WO | WO8910114 A1 | 11/1989 |
| WO | WO9007290 A1 | 7/1990 |
| WO | WO94014404 A1 | 7/1994 |
| WO | WO9534271 A1 | 12/1995 |
| WO | WO9606686 A1 | 3/1996 |
| WO | WO9911224 A2 | 3/1999 |
| WO | WO0048559 A2 | 8/2000 |
| WO | WO0147482 A1 | 7/2001 |
| WO | WO2006000257 A1 | 1/2006 |
| WO | WO2006027279 A2 | 3/2006 |
| WO | WO2006125442 A1 | 11/2006 |
| WO | WO2007010478 A2 | 1/2007 |
| WO | WO2008104655 A2 | 9/2008 |
| WO | WO 2009/090213 A1 | 11/2009 |
| WO | WO2010138266 A2 | 12/2010 |
| WO | WO2011073898 A2 | 6/2011 |
| WO | WO2011156311 A2 | 12/2011 |
| WO | WO2012038334 A1 | 3/2012 |

OTHER PUBLICATIONS

"The treatment of 11 alopecia patients with resorcinol solution", Japan, Dec. 31, 1975.

"Effects of Zinc on the New Preparation Method of Hydroxy Double Salts", Inorg. Chem. 1999, 38, 4211-4216.

"Hair care composition and method for increasing diameter of hairs", Frangrance Journal, Feb. 1992, p. 100.

All final and non-final office actions for U.S. Appl. No. 11/897,084 (P&G Case 10557MC), See Pair.

All final and non-final office actions for U.S. Appl. No. 12/393,311 (P&G Case AA752M), See Pair.

All final and non-final office actions for U.S. Appl. No. 13/527,376 (P&G Case 10557M), See Pair.

All final and non-final office actions for U.S. Appl. No. 13/633,623 (P&G Case 12268), See Pair.

All final and non-final office actions for U.S. Appl. No. 13/723,865 (P&G Case 12319), See Pair.

(56) References Cited

OTHER PUBLICATIONS

All final and non-final office actions for U.S. Appl. No. 13/871,123 (P&G Case 12457M), See Pair.
All final and non-final office actions for U.S. Appl. No. 13/871,231 (P&G Case 12458), See Pair.
All final and non-final office actions for U.S. Appl. No. 14/275,100 (P&G Case 12899), See Pair.
All final and non-final office actions for U.S. Appl. No. 14/275,225 (P&G Case 12901), See Pair.
All final and non-final office actions for U.S. Appl. No. 14/275,252 (P&G Case 12902), See Pair.
All final and non-final office actions for U.S. Appl. No. 14/825,643 (P&G Case 12268D), See Pair.
All final and non-final office actions for U.S. Appl. No. 15/195,063 (P&G Case 12899D), See Pair.
All final and non-final office actions for U.S. Appl. No. 29/419,431 (P&G Case D2009), See Pair.
All final and non-final office actions for U.S. Appl. No. 29/447,858 (P&G Case D2009D), See Pair.
Anonymous: Plantur 39 Caffeine Tonic 200ml, XP002534819, Jul. 26, 2008, URL:http://www.askshop.co.uk/shopping/plantur-39-caffeine-tonic-200ml.html.
Berger, R.S., et al., "The effects of minoxidil, 1% pyrithione zinc and a combination of both on hair density: a randomized controlled trial." British Journal of Dermatology, 2003, 149, pp. 354-362.
Courtois, M. et al., "Aging and hair cycles," British Journal of Dermatology, 1995, 132, pp. 86-93.
de Lacharriere, O. et al., "Hair Diameter Diversity," Arch Dematol., 2001, 137, pp. 641-646.
Definition of "denatured alcohol", http://worldnetweb.princeton.edu/peri/webwn?s=denatured%20alcohol, accessed Mar. 8, 2011.
Factors influencing the skin pH, Aus: pH and Skin Care, www.abw.verlag.de, 2007, pp. 45-49.
Final Report on the Safety Assessment of 4-Chloroesorincol, International Journal of Toxicology, Aug. 1996, pp. 284-294.
Gottschalck, T.E., et al., "International Cosmetic Ingredient Dictionary and Handbook," 2004, The Cosmetic, Toiletry and Fragrance Association, Washington, D.C., XP002534910, ISBN 1-882621-34-4, 10th ed., vol. 2, p. 1307, col. 1.
Hoffmann, R., "Trichoscan: Combining epiluminescence microscopy with digital image analysis for the measurement of hair growth in vivo," Eur J. Drmatol 2001; 11, pp. 362-368.
Lacarrubba, F. et al., "Videodermatoscopy Enhances Diagnostic Capability in Some Forms of Hair Loss," Am J. Clin Dermatol, 2004, 5(3), pp. 205-208.
M.P. Birch et al., "Hair density, hair diameter and the prevalence of female pattern loss," British Journal of Dermatology 2001; 144, pp. 297-304.
Olsen, EA et al., "Evaluation and treatment of male and female pattern hair loss," J. Am Acad Dermatol, vol. 52, No. 2, Feb. 2005, p. 301-311.
PCT International Search Report and Written Opinion for PCT/IB2009/050759 dated Feb. 25, 2009.
PCT International Search Report and Written Opinion for PCT/IB2009/050760 dated Aug. 5, 2009.
PCT International Search Report and Written Opinion for PCT/IB2009/050761 dated Feb. 25, 2009.
PCT International Search Report and Written Opinion for PCT/IB2009/050762 dated Feb. 25, 2009.
PCT International Search Report and Written Opinion for PCT/US2012/058560 dated Mar. 11, 2013.
PCT International Search Report and Written Opinion for PCT/US2013/038311 dated Jul. 12, 2013.
PCT International Search Report and Written Opinion for PCT/US2013/038312 dated Jul. 12, 2013.
PCT Invitation to pay additional fees for PCT/US2007/019180 dated May 3, 2008.
The Clinical Report Lansium Domesticum Jack V. Doku, vol. 23, No. 13, p. 133-146 (1989).
W. Wenner, "The Reaction of L-Ascorbic and D-Iosascorbic Acid with Nicotinic Acid and Its Amide," J. Organic Chemistry, vol. 14, pp. 22-26 (1949).

* cited by examiner

HAIR THICKENING COMPOSITIONS AND METHODS OF USE

FIELD OF THE INVENTION

The present invention relates to hair care compositions comprising one or more actives useful for increasing hair diameter and methods of use thereof.

BACKGROUND OF THE INVENTION

Many attributes contribute to the appearance of hair considered to be attractive. For instance, hair with a full and thick appearance is very desirable. In contrast, hair with a thin appearance is not as attractive, and can even lead to a perception that the thin-haired individual is older than their chronological age. Because of the foregoing problems associated with thin hair, many individuals expend great effort and time on grooming, yet still do not attain their desired hairstyle and appearance. This can lead to frustration and/or lack of confidence in his or her appearance. These problems can be experienced by both female and male consumers and at a variety of ages.

In view thereof, there is a need to provide consumers with a hair care composition that includes actives which increase hair diameter and therefore create a fuller and thicker appearance of the hair.

SUMMARY OF THE INVENTION

Provided is a method for increasing hair shaft diameter, the method including applying a hair care composition to a region of the hair, wherein the hair care composition includes from about 0.01% to about 10% of hops, wherein the hops is first extracted in glycerin; and from about 0.1% to about 10% of a rheology modifier.

Also provided is a hair care composition comprising from about 0.01% to about 10% of hops, wherein the hops is first extracted in glycerin; and from about 0.1% to about 10% of a rheology modifier.

These and other features, aspects, and advantages of the present invention will become evident to those skilled in the art from a reading of the present disclosure.

DETAILED DESCRIPTION OF EMBODIMENTS OF THE INVENTION

While the specification concludes with the claims particularly pointing and distinctly claiming the invention, it is believed that embodiments of the present invention will be better understood from the following description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitations on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

As used herein, the term "hair care compositions" are compositions that are applied to the hair and/or the skin underneath the hair, including compositions used to treat or care for the hair. Products contemplated by the phrase "hair care composition" include, but are not limited to after-shave tonics and lotions, creams, emulsions, foams, hair conditioners (rinse-off and leave-on), hair colorants, hair tonics, liquids, lotions, mousses, propellant lotions, shampoos, shave gels, temporary beard hair dyes, and the like.

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

I. Hair Care Compositions

According to an embodiment of the invention, the hair care composition may include one or more solvents, such as dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

A. Indole Compounds

The hair care compositions can further include an indole compound. As used herein, "indole compound" means one or more indoles, derivatives thereof, mixtures thereof, or salts thereof. Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

B. Xanthine Compounds

The hair care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In an embodiment, the amount of xanthine may be decreased to lessen potential white residue the may result from various formulations when the xanthine is present in higher amounts. In an embodiment, the hair care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. In an embodiment, the hair care composition may have no xanthine.

C. Vitamin $B_3$ Compounds

The hair care compositions can further include a vitamin $B_3$ compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. Accordingly, the composition may include from about 0.1% to about 25% of the vitamin $B_3$ compound; from about 0.5% to about 15% of the vitamin $B_3$ compound; or from about 3.5% to about 7.5% of the vitamin $B_3$ compound, for example, wherein the percentage is a weight percentage based on the total weight of the final hair care composition. For example, the hair care composition may further include about 2.5% of vitamin $B_3$.

D. Panthenol Compounds

The hair care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the composition may include from about 0.01% to about 5% of the panthenol compound; from about 0.03% to about 3% of the panthenol compound; from about 0.05% to about 2% of the panthenol compound; or from about 0.1% to about 1% of the panthenol compound, for example, wherein the percentage is a weight percentage based on the total weight of the final hair care composition. For example, the hair care composition may further include about 0.15% of panthenol.

According to another aspect of the present invention, the hair care compositions may be free of oleanolic acid and/or biotinyl-GHK, which is contrary to that described in U.S. Patent Application No. 20060067905.

E. Hops

In an embodiment, the hair care composition may comprise hops. The hair care composition may comprise from about 0.01% about 5% hops, alternatively from about 0.01% to about 3% hops, alternatively from about 0.01% to about 1.5% hops, and alternatively from about 0.01% to about 1% hops. In an embodiment, the hair care composition may comprise no hops.

The hops may be extracted by different methods, including extraction in glycerin, extraction in water and denatured alcohol, or extraction in propylene glycol. In an embodiment, the hops is extracted in glycerin. In an embodiment, the hops extracted in glycerin may provide improved thickening as compared to other extraction methods. In an embodiment, the hops is of the *Humulus Lupulus* species.

F. Resorcinol

In an embodiment, the hair care composition may comprise resorcinol. The hair care composition may comprise from about 1% to about 14% resorcinol, alternatively from about 1% to about 13% resorcinol, alternatively from about 1% to about 11% resorcinol, alternatively from about 1% to about 9% resorcinol, alternatively from about 1% to about 8% resorcinol, alternatively from about 1% to about 4% resorcinol, and alternatively from about 1% to about 3% resorcinol.

In an embodiment, the resorcinol may be chlorinated. In an embodiment, the resorcinol may be non-chlorinated. In an embodiment, the chlorinated resorcinol may provide improved thickening as compared to non-chlorinated resorcinol.

G. Rheology Modifier

In one embodiment, the composition comprises a rheology modifier to increase the substantivity of the composition. Any suitable rheology modifier can be used. In an embodiment, the hair care composition may comprise from about 0.1% to about 10% of a rheology modifier, alternatively from about 0.5% to about 2.2% of a rheology modifier, alternatively from about 0.7% to about 2% of a rheology modifier, and alternatively from about 1% to about 1.5% of a rheology modifier. In an embodiment, the hair care composition may comprise from about 0.5% to about 2% of a rheology modifier, alternatively from about 0.5% to about 1.9% of a rheology modifier, alternatively from about 0.5% to about 1.7% of a rheology modifier, and alternatively from about 0.5% to about 1.4% of a rheology modifier. In an embodiment, the rheology modifier may be a polyacrylamide thickener.

Non-limiting examples of rheology modifiers include acrylamide/ammonium acrylate copolymer (and)polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

H. Carrier

According to another aspect of the present invention, the hair care compositions may further include at least about 20 weight percent of an aqueous carrier. According to one embodiment, the aqueous carrier may be prepared from demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

The hair care compositions may have a pH ranging from about 3.0 to about 10, which may be measured by taking a direct pH measurement using a standard hydrogen electrode of the composition at 25° C. Accordingly, the pH of the hair care composition may be within the range from about 6 to about 9, for example.

I. Optional Ingredients

The compositions of the present invention can also additionally comprise any suitable optional ingredients as desired. For example, the composition can optionally include other active or inactive ingredients.

The compositions may include other common hair ingredients such as pyrithione zinc, minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

In one embodiment, the composition comprises a rheology modifier to increase the substantivity of the composition, such that it does not drip undesirably onto other areas of the body, onto clothing, or onto home furnishings and may also perform as a film former. Any suitable rheology modifier can be used, for example, a cellulose-based rheology modifier, such as hydroxypropylmethylcellulose. Other non-limiting examples of rheology modifiers include acrylamide/ammonium acrylate copolymer (and)polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

II. Method for Increasing Hair Shaft Diameter

The hair care composition described above may also be used in a method for increasing hair shaft diameter. The method may comprise applying the hair care composition to a region of the hair, wherein the hair care composition comprises from about 0.01% to about 10% of hops, wherein the hops is first extracted in glycerin; and from about 0.1% to about 10% of a rheology modifier.

Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Example 1

| Component | (wt %) |
| --- | --- |
| Alcohol 100% DEB 100 (Ethanol) | 50 |
| Sepigel 305 | 1.89 |
| Hops | 0.90 |
| Fragrance: Watergarden | 0.30 |
| Silicone: Abil B 8832 | 0.30 |
| Deionized water | Qs |

*Sepigel ™ 305: Polyacrylamide/C13-14 Isoparaffin/Laureth-7 from Seppic
*Hops: Humulus Lupulus (Hops) Extract 8060-28-4 from Bio-Botanica (extracted in glycerin)

Example 2

| Component | (wt %) |
| --- | --- |
| Alcohol 100% DEB 100 (Ethanol) | 58 |
| Sepigel 305 | 1.89 |
| Resorcinol | 0.15 |
| Hops | 0.9 |
| Caffeine | 0.95 |
| Niacinamide | 3.15 |
| Panthenol | 0.15 |
| Fragrance: | 0.6 |
| Amaze XT | 0.85 |
| Deionized water | Qs |

*Sepigel ™ 305: Polyacrylamide/C13-14 Isoparaffin/Laureth-7 from Seppic
*Resorcinol: 1,3-Dihydroxybenzene from Jos H Lowenstein & Sons Inc.
*Hops: Humulus Lupulus (Hops) Extract 8060-28-4 from Bio-Botanica (extracted in glycerin)
*Amaze XT: dehydroxy xanthan gum from Akzo Nobel Data

TABLE 1

| Hops [%] | Hops Type | Sepigel [%] | Average Thickness Increase [μm] | Viscosity [cps] |
|---|---|---|---|---|
| 0.9 | 1 | 1.89 | 7.5 | 14823 |
| 0.9 | 2 | 1.89 | 1.7 | 11429 |
| 0.9 | 3 | 1.89 | 1.4 | 13352 |

*Hops 1: Humulus Lupulus (Hops) Extract 8060-28-4 from Bio-Botanica (extracted in glycerin)
*Hops 2: Humulus Lupulus (Hops) Extract 8060-28-4 from IBT (extracted in water and denatured alcohol)
*Hops 3: Humulus Lupulus (Hops) Extract 8060-28-4 from Arch Chemicals, Inc. (extracted in propylene glycol)

The data in Table 1 surprisingly showed that Hops Type 1 provided a measurable average thickness increase of the hair follicle when compared to Hops Type 2 and Type 3. The Example 1 formula was used to formulate each leg, substituting different types of hops.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care compositions.

Test Methods

Measurement of Average Thickness Increase
1) Asian or Caucasian hair fibers (low-lift general population) are soaked in deionized water for 10 minutes, and allowed to equilibrate overnight in at Controlled Temperature and Humidity room (20 C, 50 RH).
2) The single hair fibers are imaged with microscope and the diameter is measured using software for baseline measurement.
3) The hair fibers are then treated with the hair care composition for 10 minutes to allow for saturation. The fibers are then removed and allowed to equilibrate and dry overnight.
4) The next day, the fibers are imaged and measured for a final reading. For each experiment, untreated control and product treatment controls are ran, and at least 5 fibers are measured per treatment.
5) In order to measure increase in thickness as a function of treatment, the final diameter is subtracted from the initial diameter. The average thickness increase is reported in the Table above, with measurements reported in micrometers.

Viscosity Test Method

The hair care composition may have a viscosity of from about 2,000 cps to about 20,000 cps, alternatively from about 10,000 cps to about 15,000 cps. The viscosity of the hair care composition may be determined by a cone and plate viscometer/rheometer which measures the viscous drag resulting from the sample material contained in the gap between a rotating cone and a stationary plate. The geometry of the cone and plate may be such that the entire sample is subjected to a uniform shear rate. A Brookfield Rheometer RS, with Cone C75-1, 26.7° C. temperature, 2.5 mL sample size, at 2 res/sec for 3 minutes may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for increasing hair shaft diameter, the method comprising applying a hair care composition to a region of the hair, wherein the hair care composition comprises:
   i. from about 0.01% to 1% of an extract of hops, by weight of the hair care composition; and
   ii. from about 0.5% to about 2.2% of a polyacrylamide thickener, by weight of the hair care composition;
   iii. at least 20% alcohol, by weight of the composition;
      wherein the extract of hops consists of a glycerin extract of hops.

2. The method of claim 1, wherein the hair care composition comprises from about 0.7% to about 2% of the polyacrylamide thickener.

3. The method of claim 1, wherein the hair care composition comprises from about 1% to about 1.5% of the polyacrylamide thickener.

4. The method of claim 1, wherein the hair care composition further comprises from about 0.01% to about 5% resorcinol.

5. The method of claim 1, wherein the hair care composition further comprises from about 0.1% to about 10% caffeine.

6. The method of claim 1, wherein the hair care composition further comprises from about 0.1% to about 25% niacinamide.

7. The method of claim 1, wherein the hair care composition further comprises from about 0.01% to about 3% panthenol.

8. The method of claim 4, wherein the resorcinol is chlorinated.

9. The method of claim 1 wherein the hair care composition is a leave-on, liquid hair care composition.

10. A method for increasing hair shaft diameter, the method comprising applying a hair care composition to a region of the hair, wherein the hair care composition comprises:
   i. from about 0.01% to 1% of an extract of hops, by weight of the hair care composition; and
   ii. from about 0.5% to about 2.2% of a polyacrylamide thickener, by weight of the hair care composition;

iii. at least 20% ethanol, by weight of the composition;
  wherein the extract of hops consists of a glycerin extract of hops;
  wherein the hops comprise the species *Humulus lupulus*.

* * * * *

UNITED STATES PATENT AND TRADEMARK OFFICE
CERTIFICATE OF CORRECTION

PATENT NO.        : 10,123,966 B2
APPLICATION NO.   : 14/275196
DATED             : November 13, 2018
INVENTOR(S)       : Goher Mahmud et al.

It is certified that error appears in the above-identified patent and that said Letters Patent is hereby corrected as shown below:

On the Title Page

Under item (*) Notice Line 4, the following language should be included:
"This patent is subject to a terminal disclaimer."

Signed and Sealed this
Twenty-ninth Day of January, 2019

Andrei Iancu
*Director of the United States Patent and Trademark Office*